(12) United States Patent
Miyauchi

(10) Patent No.: US 9,612,178 B2
(45) Date of Patent: Apr. 4, 2017

(54) PARTICLE MONITORING METHOD AND PARTICLE MONITORING SYSTEM

(75) Inventor: Kunio Miyauchi, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 529 days.

(21) Appl. No.: 14/237,422

(22) PCT Filed: Aug. 8, 2012

(86) PCT No.: PCT/JP2012/070205
§ 371 (c)(1),
(2), (4) Date: Feb. 6, 2014

(87) PCT Pub. No.: WO2013/022023
PCT Pub. Date: Feb. 14, 2013

(65) Prior Publication Data
US 2014/0182357 A1   Jul. 3, 2014

Related U.S. Application Data

(60) Provisional application No. 61/531,132, filed on Sep. 6, 2011.

(30) Foreign Application Priority Data

Aug. 9, 2011 (JP) .................................. 2011-173888

(51) Int. Cl.
*G01M 15/10* (2006.01)
*H01L 21/67* (2006.01)
(Continued)

(52) U.S. Cl.
CPC ....... *G01M 15/102* (2013.01); *C23C 16/4412* (2013.01); *C23C 16/52* (2013.01); *G01N 15/0205* (2013.01); *H01L 21/67253* (2013.01)

(58) Field of Classification Search
CPC ................ B08B 3/12; H01J 37/32862; H01L 21/67028; H01L 21/6831; H01L 21/67069;
(Continued)

(56) References Cited

U.S. PATENT DOCUMENTS 5,974,868 A * 11/1999 Decain ...................... B08B 3/00
340/627
6,197,123 B1 * 3/2001 Poag ................... C23C 16/4405
134/18
(Continued)

FOREIGN PATENT DOCUMENTS

JP       10-326812 A    12/1998
JP       2005-101539 A   4/2005
(Continued)

OTHER PUBLICATIONS

International Search Report for PCT/JP2012/070205 dated Sep. 11, 2012.

*Primary Examiner* — Daniel S Larkin
*Assistant Examiner* — Jamar Ray
(74) *Attorney, Agent, or Firm* — Pearne & Gordon LLP

(57) ABSTRACT

A particle monitoring method of monitoring particles included in an exhaust gas from a depressurized processing vessel 12 includes counting the particles included in the exhaust gas from the depressurized processing vessel 12 while cleaning an inside of the depressurized processing vessel 12 by a particle monitor 18; creating a histogram showing a time and the number of particles from a result of the counting of the particles; extracting, from the histogram, a first feature amount indicating a correlation between a mode of the number of the particles and a particle counting period; and extracting, from the histogram, a second feature amount indicating a correlation between the particle count- (Continued)

ing period and a distribution tendency of the particles during the particle counting period.

16 Claims, 9 Drawing Sheets

(51) Int. Cl.
*C23C 16/44* (2006.01)
*C23C 16/52* (2006.01)
*G01N 15/02* (2006.01)

(58) Field of Classification Search
CPC ........... H01L 21/67253; C23C 16/4412; C23C 16/52; G01M 15/102; G01N 15/0205
See application file for complete search history.

(56) References Cited

U.S. PATENT DOCUMENTS

| | | | | |
|---|---|---|---|---|
| 8,043,438 B2* | 10/2011 | Sakai | ................. | C23C 16/4405 134/1.1 |
| 8,337,629 B2* | 12/2012 | Moriya | .................... | B08B 3/12 134/1 |
| 2001/0011548 A1* | 8/2001 | Tanaka | .................... | B08B 3/102 134/18 |
| 2002/0029791 A1* | 3/2002 | Matsuoka | ........... | C23C 16/4407 134/18 |
| 2006/0132769 A1* | 6/2006 | Iwa | .................... | G01N 15/1434 356/336 |
| 2006/0141782 A1* | 6/2006 | Hasebe | ............... | C23C 16/4408 438/680 |
| 2009/0038645 A1* | 2/2009 | Nomura | .................... | B08B 3/04 134/18 |
| 2009/0299652 A1* | 12/2009 | Nakayama | ........ | H01L 21/67069 702/26 |
| 2013/0000280 A1* | 1/2013 | Korenev | ............ | G01N 15/0656 60/276 |

FOREIGN PATENT DOCUMENTS

| | | |
|---|---|---|
| JP | 2005-317900 A | 11/2005 |
| JP | 2009-290086 A | 12/2009 |

* cited by examiner

FIG. 6

|  | EQUAL TO OR LARGER THAN THRESHOLD VALUE | | SMALLER THAN THRESHOLD VALUE | |
|---|---|---|---|---|
|  | SMALL FEATURE AMOUNT X | LARGE FEATURE AMOUNT X | SMALL FEATURE AMOUNT X | LARGE FEATURE AMOUNT X |
| SMALL FEATURE AMOUNT Y | INCREASE PURGE GAS INCREASE HIGH VOLTAGE | INCREASE HIGH VOLTAGE | INCREASE PURGE GAS | - |
| LARGE FEATURE AMOUNT Y | INCREASE PURGE GAS INCREASE HIGH VOLTAGE | INCREASE HIGH VOLTAGE | - | INCREASE HIGH VOLTAGE |

FIG. 9

| SAMPLE NO. | FEATURE AMOUNT X | FEATURE AMOUNT Z | PCS1 | PCS2 | CLUSTER |
|---|---|---|---|---|---|
| 1 | 56 | 97.7 | 2.8 | -1.1 | 1 |
| 2 | 54 | 100 | 2.8 | -0.9 | 1 |
| 3 | 50 | 100 | 2.6 | -0.7 | 1 |
| 4 | 51.3 | 94.4 | 2.5 | -0.9 | 1 |
| 5 | 53 | 91.1 | 2.5 | -1.1 | 1 |
| 6 | 51.9 | 90.3 | 2.4 | -1.1 | 1 |
| 7 | 48.1 | 91.7 | 2.2 | -0.8 | 1 |
| 8 | 47.2 | 84.6 | 2 | -1 | 1 |
| 9 | 44.8 | 86.3 | 1.9 | -0.8 | 1 |
| 10 | 41.1 | 82.3 | 1.7 | -0.7 | 1 |
| 11 | 42.1 | 76.3 | 1.6 | -0.9 | 1 |
| 12 | 47.5 | 53.8 | 1.3 | -1.8 | 1 |
| 13 | 19 | 100 | 1 | 0.8 | 2 |
| 14 | 17 | 100 | 0.9 | 0.9 | 2 |
| 15 | 12.2 | 99.1 | 0.6 | 1.1 | 2 |
| 16 | 7 | 100 | 0.4 | 1.4 | 2 |
| 17 | 7 | 100 | 0.4 | 1.4 | 2 |
| 18 | 7 | 100 | 0.4 | 1.4 | 2 |
| 19 | 6 | 100 | 0.4 | 1.5 | 2 |
| 20 | 8.1 | 94.9 | 0.3 | 1.2 | 2 |
| 21 | 5 | 100 | 0.3 | 1.5 | 2 |
| 22 | 7 | 95.7 | 0.3 | 1.3 | 2 |
| 23 | 7.1 | 94.9 | 0.3 | 1.3 | 2 |
| 24 | 6.1 | 96.6 | 0.3 | 1.4 | 2 |
| 25 | 7.1 | 92.7 | 0.2 | 1.2 | 2 |
| 26 | 7.4 | 91.3 | 0.2 | 1.2 | 2 |
| 27 | 7 | 91.1 | 0.2 | 1.2 | 2 |
| 28 | 7.2 | 90.6 | 0.2 | 1.2 | 2 |
| 29 | 7.8 | 89.4 | 0.2 | 1.1 | 2 |
| 30 | 6.1 | 91.8 | 0.1 | 1.3 | 2 |
| 31 | 7.2 | 86.7 | 0.1 | 1.1 | 2 |
| 32 | 4.1 | 92 | 0.1 | 1.4 | 2 |
| 33 | 17.6 | 76.3 | 0.3 | 0.3 | 3 |
| 34 | 6.4 | 84.6 | 0 | 1.1 | 3 |
| 35 | 6.8 | 83.3 | 0 | 1 | 3 |
| 36 | 14.1 | 68.8 | 0 | 0.3 | 3 |
| 37 | 6.1 | 84.4 | 0 | 1.1 | 3 |
| 38 | 9.4 | 77.3 | -0.1 | 0.7 | 3 |
| 39 | 8.5 | 76.8 | -0.1 | 0.8 | 3 |
| 40 | 10.4 | 72.2 | -0.1 | 0.5 | 3 |
| 41 | 6.3 | 78.9 | -0.2 | 0.9 | 3 |
| 42 | 7.8 | 75.5 | -0.2 | 0.8 | 3 |
| 43 | 4.8 | 76.3 | -0.3 | 1 | 3 |
| 44 | 2.4 | 82.9 | -0.3 | 1.2 | 3 |
| 45 | 12.5 | 62.2 | -0.3 | 0.2 | 3 |
| 46 | 6.8 | 72.2 | -0.3 | 0.7 | 3 |
| 47 | 6.8 | 69 | -0.4 | 0.6 | 3 |
| 48 | 2.8 | 70.6 | -0.6 | 0.9 | 3 |
| 49 | 26.9 | 73.6 | 0.7 | -0.2 | 4 |
| 50 | 24.7 | 66.7 | 0.4 | -0.3 | 4 |
| 51 | 29.4 | 50 | 0.2 | -1 | 4 |
| 52 | 19.1 | 47.4 | -0.3 | -0.5 | 4 |
| 53 | 23.1 | 36.2 | -0.4 | -1 | 4 |
| 54 | 28.4 | 25 | -0.4 | -1.8 | 4 |
| 55 | 19.4 | 43.9 | -0.5 | -0.6 | 4 |
| 56 | 12.7 | 54.2 | -0.5 | 0 | 4 |
| 57 | 18.6 | 39.2 | -0.6 | -0.7 | 4 |
| 58 | 16.3 | 43.4 | -0.6 | -0.5 | 4 |
| 59 | 27.6 | 21.3 | -0.6 | -1.6 | 4 |
| 60 | 23.6 | 28.6 | -0.6 | -1.2 | 4 |
| 61 | 9.9 | 54.4 | -0.6 | 0.1 | 4 |
| 62 | 6.7 | 59.4 | -0.7 | 0.4 | 4 |
| 63 | 17.7 | 35.7 | -0.7 | -0.7 | 4 |
| 64 | 21.1 | 29 | -0.7 | -1.1 | 4 |
| 65 | 17.3 | 35.8 | -0.7 | -0.7 | 4 |
| 66 | 15.6 | 38.5 | -0.7 | -0.6 | 4 |
| 67 | 13.8 | 41.9 | -0.7 | -0.4 | 4 |
| 68 | 6.4 | 55.7 | -0.8 | 0.3 | 4 |
| 69 | 19.4 | 29.8 | -0.8 | -1 | 4 |
| 70 | 19.2 | 30.2 | -0.8 | -1 | 4 |
| 71 | 16.7 | 30.8 | -0.8 | -0.9 | 4 |
| 72 | 19.2 | 29.5 | -0.8 | -1 | 4 |
| 73 | 18.3 | 31.3 | -0.8 | -0.9 | 4 |
| 74 | 6.5 | 53.8 | -0.8 | 0.3 | 4 |
| 75 | 16.8 | 32.6 | -0.8 | -0.8 | 4 |
| 76 | 15.4 | 31.8 | -0.9 | -0.7 | 4 |
| 77 | 4.5 | 52.9 | -0.9 | 0.4 | 4 |
| 78 | 17.7 | 25 | -1 | -1 | 4 |
| 79 | 9 | 42 | -1 | -0.2 | 4 |
| 80 | 16.9 | 26.3 | -1 | -0.9 | 4 |
| 81 | 5.4 | 45.8 | -1.1 | 0.1 | 4 |
| 82 | 10.1 | 36.5 | -1.1 | -0.3 | 4 |
| 83 | 15.4 | 35.9 | -1.1 | -0.6 | 4 |
| 84 | 12.4 | 28.6 | -1.2 | -0.7 | 4 |
| 85 | 11 | 30.1 | -1.2 | -0.6 | 4 |
| 86 | 16 | 10.1 | -1.4 | -1.3 | 4 |
| 87 | 8.5 | 24.6 | -1.4 | -0.8 | 4 |
| 88 | 12.6 | 15.8 | -1.5 | -1 | 4 |
| 89 | 7.3 | 23.3 | -1.5 | -0.5 | 4 |

PARTICLE MONITORING METHOD AND PARTICLE MONITORING SYSTEM

CROSS-REFERENCE TO RELATED APPLICATION

This Application is a U.S. national phase application under 35 U.S.C. §371 of PCT Application No. PCT/JP2012/070205 filed on Aug. 8, 2012, which claims the benefit of Japanese Patent Application No. 2011-173888 filed on Aug. 9, 2011, and U.S. Provisional Application Ser. No. 61/531,132 filed on Sep. 6, 2011, the entire disclosures of which are incorporated herein by reference.

TECHNICAL FIELD

The embodiments described herein pertain generally to a particle monitoring method and a particle monitoring system.

BACKGROUND ART

In a manufacturing process of a semiconductor device, various kinds of film forming processes of forming, e.g., insulating films, an etching process of etching, e.g., these insulating films, and so forth are performed in a depressurized processing vessel provided in a substrate processing apparatus such as a plasma processing apparatus. In this depressurized processing vessel, fine particles caused by, for example, sputtering of plasma generated in the processing vessel or resulted from reaction products generated by a reactant gas may adhere to the inside of the depressurized processing vessel. If these particles adhere to a substrate, a production yield may be deteriorated. In order to solve this problem, the substrate processing apparatus is required to have high degree of cleanliness.

As a way to clean the inside of the processing vessel, Patent Document 1, for example, describes a method of dispersing particles within the processing vessel by using a shock wave of a gas generated when the gas is introduced into the processing vessel, an electromagnetic stress generated when a high voltage is applied, or the like.

Further, as a way to evaluate the cleanliness within the processing vessel, there is proposed, for example, a method of supplying a purge gas into the processing vessel and counting particles separated from the processing vessel due to the supply of the purge gas by using a particle monitor (Patent Document 2).

Just by counting the particles, however, it is difficult to identify a particle source from which the particles are generated. Thus, a generation amount of the particles cannot be reduced. For this reason, typically, in the aforementioned substrate processing apparatus, analysis of components of the particles adhering to the substrate or analysis of distribution of each component on the substrate has been conducted in order to identify the particle source (Patent Document 3).

Patent Document 1: Japanese Patent Laid-open Publication No. 2005-101539
Patent Document 2: Japanese Patent Laid-open Publication No. 2005-317900
Patent Document 3: Japanese Patent Laid-open Publication No. H10-326812

DISCLOSURE OF THE INVENTION

Problems to be Solved by the Invention

However, in order to identify the particle source based on the distribution of the particles on the substrate or the like, advanced expertise and experience in a substrate process and a substrate processing apparatus are required. Depending on the mastery of operators, there may be errors in their determination results.

Further, analyzing the distribution of the particles may be more difficult than analyzing the components or the number of the particles, and it is very difficult to understand the characteristic of the particle distribution. Accordingly, it may also be very difficult to determine abnormality thereof. For this reason, a method of setting a condition of a gas to be supplied when cleaning the inside of the processing vessel or a method of determining timing for disassembling and managing the processing vessel is yet to be established. That is, the method of cleaning the processing vessel is not optimized yet.

In view of the foregoing problems, example embodiments provide a method and an apparatus for appropriately monitoring particles within a depressurized processing vessel configured to perform a process on the substrate therein.

Means for Solving the Problems

In one example embodiment, a particle monitoring method monitors particles included in an exhaust gas from a depressurized processing vessel, in which a process is performed on a substrate, when cleaning an inside of the depressurized processing vessel by dispersing the particles through processes of supplying a purge gas into the depressurized processing vessel to apply a shock wave, and then, supplying a high voltage intermittently to apply an electromagnetic stress to the depressurized processing vessel. The particle monitoring method includes counting the particles included in the exhaust gas from the depressurized processing vessel while cleaning the inside of the depressurized processing vessel by a counting unit; creating a histogram showing a relationship between time and the number of the particles from a result of the counting of the particles; extracting, from the histogram, a first feature amount indicating a correlation between a mode of the number of the particles and a particle counting period; and extracting, from the histogram, a second feature amount indicating a correlation between the particle counting period and a distribution tendency of the particles during the particle counting period.

According to the example embodiment, the first feature amount extracted from a relationship between a mode of the number of the particles and a particle counting period and the second feature amount extracted from a relationship between the particle counting period and a distribution tendency of the particles during the particle counting period can be obtained. Thus, by comparing the first feature amount and the second feature amount, it is possible to quantitatively investigate the tendency of the particles exhausted from the depressurized processing vessel during the cleaning process of the depressurized processing vessel, more specifically, whether particles to be dispersed by the shock wave of the purge gas are dominant or whether particles to be dispersed by the electromagnetic stress are dominant. Accordingly, it may be possible to appropriately monitor the particles within the depressurized processing vessel.

In another example embodiment, a particle monitoring method monitors particles included in an exhaust gas from a depressurized processing vessel, in which a process is performed on a substrate, when cleaning an inside of the depressurized processing vessel by dispersing the particles through processes of supplying a purge gas into the depressurized processing vessel to apply a shock wave, and then, supplying a high voltage intermittently to apply an electromagnetic stress to the depressurized processing vessel. The particle monitoring method includes counting the particles included in the exhaust gas from the depressurized processing vessel while cleaning the inside of the depressurized processing vessel by a counting unit; creating a histogram showing a relationship between time and the number of the particles from a result of the counting of the particles; extracting, from the histogram, a first feature amount indicating a correlation between a mode of the number of the particles and a particle counting period; extracting, from the histogram, a second feature amount indicating a correlation between the total number of the particles counted during the particle counting period and the number of the particles at the mode; performing the extracting of the first feature amount and the extracting of the second feature amount whenever the process is performed on the substrate in the depressurized processing vessel; calculating a principal component load of each of the first feature amount and the second feature amount by performing a principal component analysis in which the first feature amounts and the second feature amounts are set as variables; calculating a principal component score of each of the first feature amount and the second feature amount based on each principal component load; and performing a cluster analysis for the principal component scores and estimating a state of particle adhesion within the depressurized processing vessel based on a result of the performing of the cluster analysis.

In still another example embodiment, a particle monitoring system monitors particles included in an exhaust gas from a depressurized processing vessel, in which a process is performed on a substrate, when cleaning an inside of the depressurized processing vessel by dispersing particles through processes of supplying a purge gas into the depressurized processing vessel to apply a shock wave, and then, supplying a high voltage intermittently to apply an electromagnetic stress to the depressurized processing vessel. The particle monitoring system includes a counting unit configured to count the particles included in the exhaust gas from the depressurized processing vessel while cleaning the inside of the depressurized processing vessel; an operation unit configured to create a histogram showing a relationship between time and the number of the particles from a result of the counting of the particles; and an extracting unit configured to extract, from the histogram, a first feature amount indicating a correlation between a mode of the number of the particles and a particle counting period, and configured to extract, from the histogram, a second feature amount indicating a correlation between the particle counting period and a distribution tendency of the particles during the particle counting period.

In still another example embodiment, a particle monitoring system monitors particles included in an exhaust gas from a depressurized processing vessel, in which a process is performed on a substrate, when cleaning an inside of the depressurized processing vessel by dispersing particles through processes of supplying a purge gas into the depressurized processing vessel to apply a shock wave, and then, supplying a high voltage intermittently to apply an electromagnetic stress to the depressurized processing vessel. The particle monitoring system includes a counting unit configured to count the particles included in the exhaust gas from the depressurized processing vessel while cleaning the inside of the depressurized processing vessel; an operation unit configured to create a histogram showing a relationship between time and the number of the particles from a result of the counting of the particles; an extracting unit configured to extract, from the histogram, a first feature amount indicating a correlation between a mode of the number of the particles and a particle counting period, and configured to extract, from the histogram, a second feature amount indicating a correlation between the total number of the particles counted during the particle counting period and the number of the particles at the mode; an analyzing unit configured to calculate a principal component load of each of the first feature amount and the second feature amount by performing a principal component analysis in which the first feature amounts and the second feature amounts extracted whenever the process is performed on the substrate in the depressurized processing vessel are set as variables; a calculating unit configure to calculate a principal component score of each of the first feature amount and the second feature amount based on each principal component load; and an estimating unit configured to perform a cluster analysis of for the principal component scores and estimate a state of particle adhesion within the depressurized processing vessel based on a result of the cluster analysis.

Effect of the Invention

In accordance with example embodiments, it is possible to appropriately monitor particles within a depressurized processing vessel in which a process is performed on the substrate therein. As a result, cleaning of the depressurized processing vessel can be performed under appropriate conditions.

BRIEF DESCRIPTION OF THE DRAWINGS

FIG. 6 is a table showing contents of changes of the cleaning sequence.

FIG. 9 is a table showing feature amounts accumulated in an accumulator.

DETAILED DESCRIPTION

Figure 1:
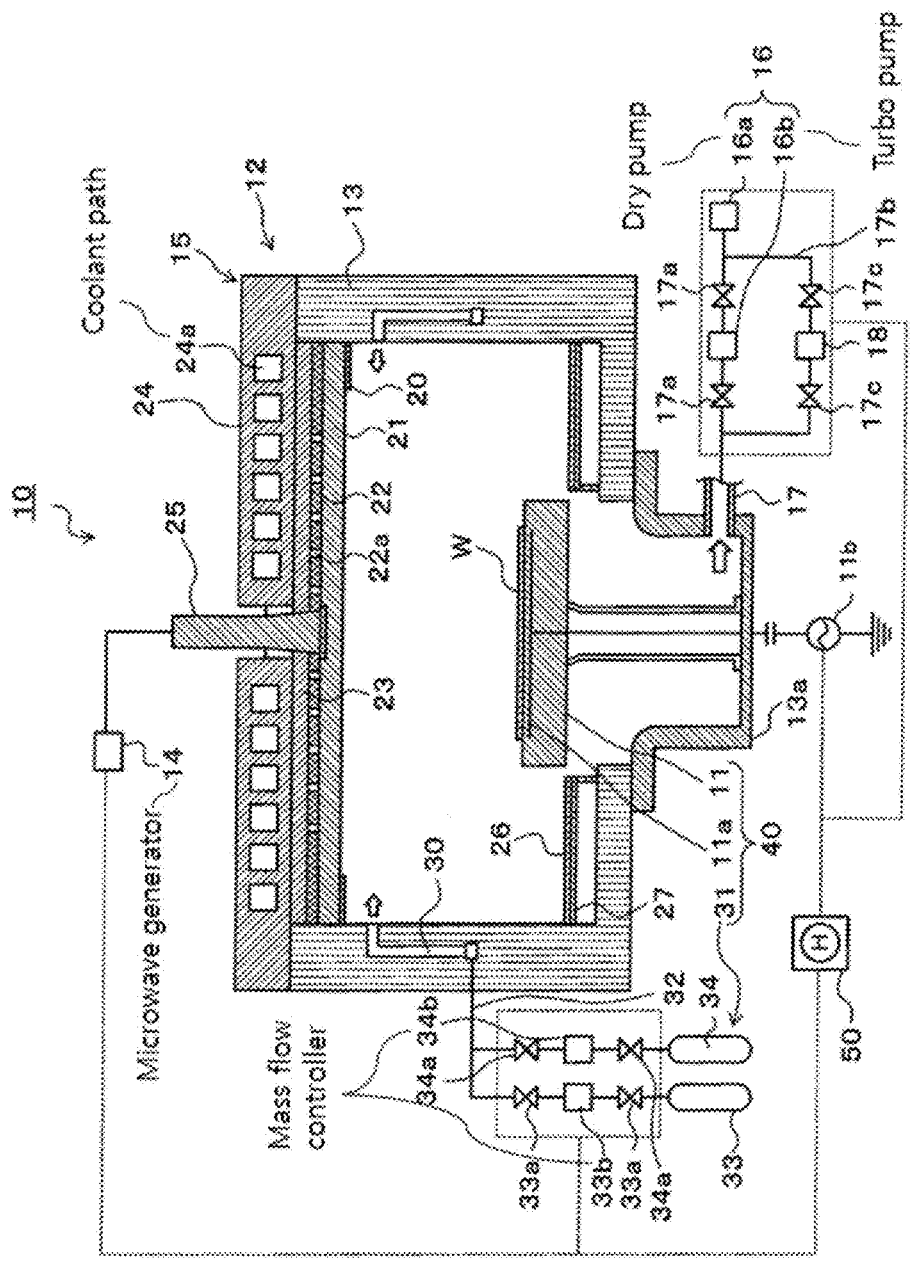
FIG. 1 is a schematic longitudinal cross sectional view illustrating an example configuration of a substrate processing system in accordance with an example embodiment.

In the following, example embodiments will be described, and reference is made to the accompanying drawings, which form a part of the description. FIG. 1 is a longitudinal cross sectional view illustrating a schematic configuration of a substrate processing system 10 including a particle monitoring system 1 in accordance with an example embodiment. The substrate processing system 10 in accordance with the present example embodiment is, for example, a plasma processing system configured to perform an etching process or a film forming process on a wafer W by exciting a processing gas supplied into the apparatus into plasma with a microwave.

The substrate processing system 10 includes a depressurized processing vessel 12 in which a susceptor 11 serving as a mounting table configured to mount thereon a wafer W is provided. The depressurized processing vessel 12 includes a main body 13 having a top opening corresponding to the wafer W held on the susceptor 11; and a microwave supplying unit 15 that closes the top opening of the main body 13 and is configured to supply a microwave of, e.g., about 2.45 GHz into the depressurized processing vessel 12. The microwave is generated by a microwave generator 14.

The susceptor 11 includes an electrode 11a embedded therein, and the electrode 11a is connected to a power supply 11b configured to supply a voltage to the electrode 11a to attract and hold the wafer W. Further, the power supply 11b is configured to apply high voltages of, e.g., about ±1 kV alternately to the electrode 11a. With this configuration, by applying the high voltages from the power supply 11b intermittently, an electromagnetic stress may be generated in the depressurized processing vessel 12, and particles adhering to the inside of the depressurized processing vessel 12 may be dispersed.

A gas exhaust chamber 13a is provided at a bottom portion of the main body 13. A gas exhaust line 17 led to a gas exhaust device 16 is connected to the gas exhaust chamber 13a.

The gas exhaust device 16 includes a dry pump 16a configured to preliminarily evacuate the inside of the depressurized processing vessel 12 to a low vacuum level; and a turbo pump 16b for obtaining a high vacuum level when performing a plasma process on the wafer W. The turbo pump 16b is provided upstream of the dry pump 16a at the gas exhaust line 17. Control valves 17a configured to control a gas exhaust amount in the gas exhaust line 17 and block a gas exhaust is provided upstream and downstream of the turbo pump 16b, respectively. Further, a bypass line 17b formed to bypass the turbo pump 16b is connected to each control valve 17a.

The bypass line 17b is equipped with a particle monitor 18 as a counting device configured to count particles included in an exhaust gas from the depressurized processing vessel 12. At the bypass line 17b, bypass valves 17c are provided upstream and downstream of the particle monitor 18, respectively. With this configuration, by manipulating the control valves 17a and the bypass valves 17c, it is possible to switch a gas exhaust system from the depressurized processing vessel 12 between the gas exhaust line 17 and the bypass line 17b.

The particle monitor 18 includes a light source (not shown) configured to irradiate laser light into the bypass line 17b; and a light receiving unit (not shown) configured to receive laser light scattered by particles in the bypass line 17b and convert the received laser light into an electric signal. The electric signal converted by the light receiving unit may be inputted to a controller 50 to be described later.

The microwave supplying unit 15 includes a microwave transmitting plate 21, a slot plate 22, a dielectric plate 23 and a metal plate 24. The microwave transmitting plate 21 is supported at a supporting member 20, which is inwardly protruded from the main body 13, via a seal member such as an 0-ring for securing airtightness. The slot plate 22 is provided on a top surface of the microwave transmitting plate 21 and serves as an antenna. The dielectric plate 23 is provided on a top surface of the slot plate 22 and serves as a wavelength shortening plate. The metal plate 24 is provided on a top surface of the dielectric plate 23. A coaxial waveguide 25 is connected to a center of the microwave supplying unit 15, and the microwave generator 14 is connected to the coaxial waveguide 25. The microwave transmitting plate 21 and the dielectric plate 23 may be made of, but not limited to, a dielectric material such as quartz, alumina or aluminum nitride. The slot plate 22 may be formed of a thin circular plate made of, but not limited to, a conductive material such as copper, aluminum or nickel and is configured as a so-called radial line slot antenna having a multiple number of slots 22a concentrically formed on a surface thereof. A coolant path 24a through which a coolant is flown is formed within the plate 24.

A gas baffle plate 26 made of, but not limited to, quartz is provided around the susceptor 11 in the depressurized processing vessel 12. The gas baffle plate 26 is supported on a supporting member 27 which is made of, but not limited to, aluminum.

Gas supply openings 30 configured to supply a gas into the depressurized processing vessel 12 are formed in an upper inner peripheral surface of the main body 13 of the depressurized processing vessel 12. By way of example, the gas supply openings 30 are formed at plural positions along the inner peripheral surface of the depressurized processing vessel 12. The gas supply openings 30 are connected to, for example, a gas supply line 32 communicating with a gas supplying unit 31 provided outside the depressurized processing vessel 12. In the present example embodiment, the gas supplying unit 31 includes a rare gas supply unit 33 configured to supply a rare gas for plasma generation; and a purge gas supply unit 34 configured to supply a purge gas for purging the inside of the depressurized processing vessel 12 after the wafer W is processed. Further, the gas supplying unit 31 also includes valves 33a and a mass flow controller 33b provided between the gas supply unit 33 and the gas supply openings 30, and valves 34a and a mass flow controller 34b provided between the gas supply unit 34 and the gas supply openings 30. Flow rates of the gases supplied through the gas supply openings 30 are controlled by the mass flow controllers 33b and 34b.

The purge gas supply unit 34 is capable of supplying the purge gas into the depressurized processing vessel 12 at a flow rate higher than a flow rate in a conventional purging process performed after the wafer W is processed. By way of non-limiting example, the purge gas may be supplied at a high flow rate of about 70 L/min (about 70000 SCCM). By supplying the purge gas at such a high flow rate, the purge gas is rapidly introduced into the depressurized processing vessel 12, so that a shock wave is applied to the inside of the depressurized processing vessel 12 and particles adhering to the inside of the depressurized processing vessel 12 may be dispersed. Further, the electrode 11a embedded in the susceptor 11, the power supply 11b and the gas supplying unit 31 form a cleaning unit 40 configured to clean the inside of the depressurized processing vessel 12.

Figure 2:
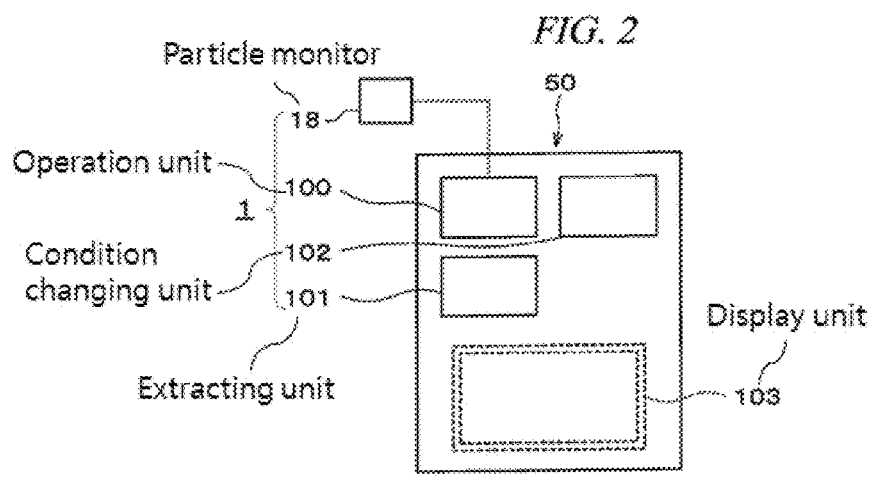
FIG. 2 is an explanatory diagram illustrating a schematic configuration of a controller.

The above-described substrate processing system 10 include the controller 50. The controller 50 may include, as depicted in FIG. 2, an operation unit 100 configured to create a histogram based on a counting result of the particles by the particle monitor 18; an extracting unit 101 configured to extract a feature amount from the histogram; and a condition changing unit 102 configured to change conditions for the cleaning by the cleaning unit 40 based on the feature amount extracted from the extracting unit 101. The operation unit 100, the extracting unit 101, the condition changing unit 102 and the particle monitor 18 form the particle monitoring system 1 in accordance with the present example embodiment.

The controller 50 may be implemented by a computer having, for example, a CPU or a memory. As the controller 50 executes a program stored in, for example, the memory, a substrate process in the substrate processing system 10 or cleaning of the inside of the depressurized processing vessel 12 by the cleaning unit 40 may be performed. Further, various kinds of programs for implementing a substrate process or a substrate transfer in the substrate processing system 10 may be stored on a computer-readable storage medium H such as, but not limited to, a hard disk (HD), a flexible disk (FD), a compact disk (CD), a magnetic optical disk (MO) or a memory card, and may be installed on the controller 50 from the storage medium H.

Figure 3:
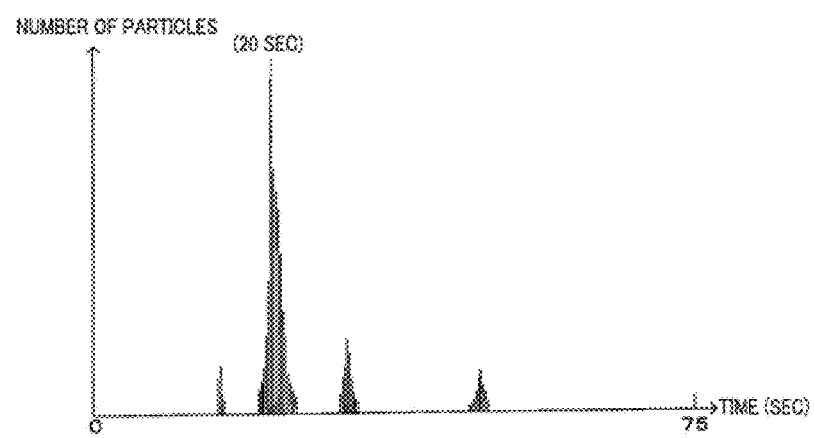
FIG. 3 is a histogram showing a relationship between the number of particles and time.

The number of particles counted by the particle monitor 18, e.g., the number of particles per a unit time is inputted as an electrical signal to the operation unit 100 via the controller 50. Based on the inputted electrical signal, the operation unit 100 creates a histogram showing a relationship between the number of particles and time, as shown in FIG. 3, for example. On the histogram in FIG. 3, a horizontal axis represents time and a vertical axis represents the number of particles.

The extracting unit 101 analyzes a distribution tendency of the number of particles on the histogram created by the operation unit 100, and extracts a first feature amount X representing a correlation between a mode (most frequent value) of the number of particles and a counting period of the particles. The first feature amount X may be represented by the following equation (1), for example.

$$X = \frac{\sum_{i=0}^{T} t \times P_t}{\sum_{i=0}^{T} P_t} \quad (1)$$

In the equation (1), T denotes a counting period of the particles; t, a measurement time; $P_t$, the number of particles at the measurement time.

Figure 4:
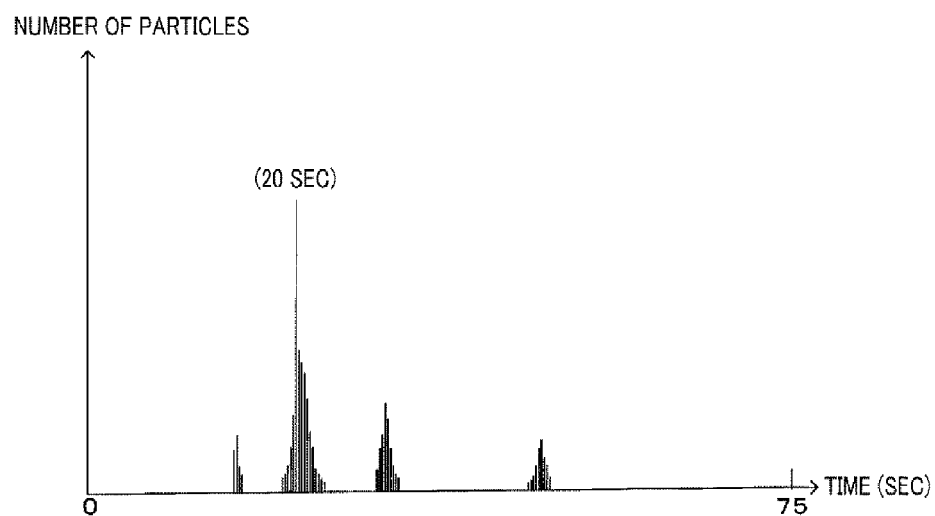
FIG. 4 is a histogram showing a relationship between the number of particles and time.

As can be seen from the equation (1), the first feature amount X is calculated by weighted-averaging the measurement time t, i.e., the time when the particles are measured, over the number of particles measured at that measurement time t. The first feature amount X indicates a tendency regarding in which time range in a cleaning sequence to be described later the mode of the number of particles is distributed. The time calculated by the first feature amount X may not necessarily coincide with the mode. By way of example, on the histogram of FIG. 3, the mode is '20 seconds,' whereas the first feature amount X calculated according to the equation (1) is, e.g., '21.1 seconds.' The discrepancy between the first feature amount X and the mode may increase as the number of particles at the mode is decreased, for example. To elaborate, as shown in FIG. 4, for example, on a histogram where only the number of particles at a mode is smaller than that of FIG. 3 and the other numbers of particles are the same as those of FIG. 3, a first feature amount X is larger than the first feature amount in FIG. 3.

Further, the extracting unit 101 is configured to extract, from the histogram, a second feature amount Y indicating a correlation between the counting period of the particles and the distribution tendency of the particles during the counting period. The second feature amount Y may be represented by the following equation (2).

$$Y = \frac{\sum_{i=0}^{T} t \times D(t)}{\sum_{i=0}^{T} D(t)} \left\{ \begin{array}{l} P_t = 0 \\ P_t > 0 \end{array} \middle| \begin{array}{l} D(t) = 0 \\ D(t) = 1 \end{array} \right\} \quad (2)$$

In the equation (2), $P_t$ denotes the number of particles at a measurement time, and the value of D(t) is '1' when $P_t$ is larger than zero, i.e., when particles are counted at the measurement time t, whereas the value of D(t) is '0' when $P_t$ is zero.

The second feature amount Y calculated by the equation (2) is obtained by simple-averaging the measurement time when the particles are observed. The second feature amount Y indicates, regardless of whether the number of particles is large or small, a tendency regarding in which time range in the cleaning sequence to be described later the particles are observed. Accordingly, the second feature amount Y calculated from the histogram shown in FIG. 3 and the second feature amount Y calculated from the histogram shown in FIG. 4 are same. The second feature amount Y calculated from FIG. 3 and FIG. 4 is, for example, about '27.3 seconds.'

Figure 5:
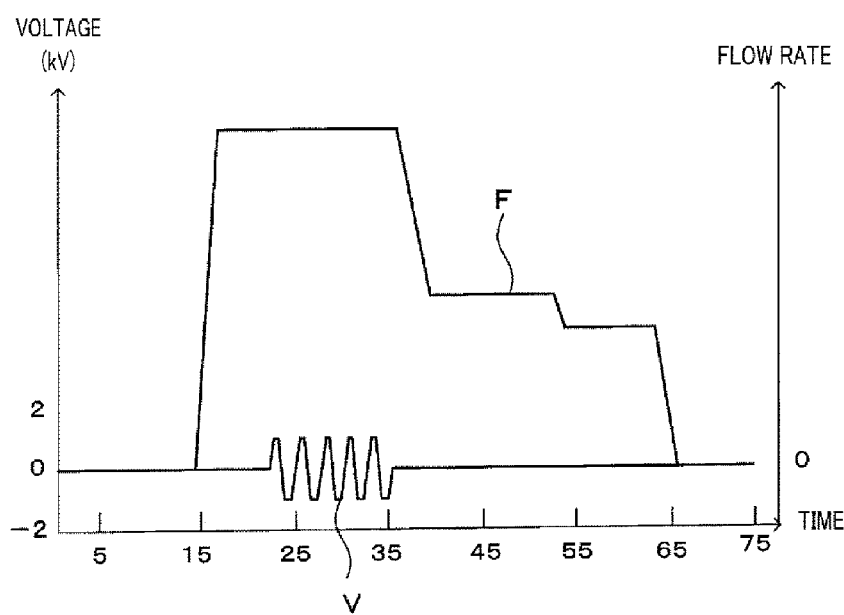
FIG. 5 is a graph showing an example of a cleaning sequence.

The cleaning sequence, as shown in FIG. 5, to be performed in the depressurized processing vessel 12 by the cleaning unit 40 is inputted to the condition changing unit 102 in advance. In FIG. 5, a horizontal axis represents time and a vertical axis represents a voltage and a flow rate of a purge gas. FIG. 5 shows changes of a voltage (V) and a flow rate (F) of the purge gas after the counting of the number of particles is started in the particle monitor 18. In this cleaning sequence, the purge gas is first supplied into the depressurized processing vessel 12 with the lapse of about 15 seconds after the counting of the number of particles is started in the particle monitor 18. Then, after 7 seconds elapses from then, the power supply 11b applies a high voltage of about ±1 kV to the electrode 11a for about 18 seconds, while inverting the polarity thereof at a cycle of, e.g., about 1 second.

Then, in the condition changing unit 102, conditions of this cleaning sequence are changed based on the first feature amount X and the second feature amount Y. The change of the cleaning sequence in the condition changing unit 102 will be elaborated below.

As stated above, a tendency of the time range when the particles are generated in a great amount can be found from the first feature amount X. However, the value of the first feature amount X may be increased or decreased depending on the time range when the particles are observed in a great amount. Further, the value of the first feature amount X may be increased or decreased as the number of particles near the mode is varied, as shown in FIG. 3 and FIG. 4. Accordingly, it may be difficult to accurately investigate the tendency of the particles dispersed from the depressurized processing vessel 12. Meanwhile, the distribution tendency of the particles during the counting period by the particle monitor 18 can be found from the second feature amount Y, regardless of whether the number of particles is large or small. Accordingly, if the first feature amount X is larger than the second feature amount Y, for example, it may indicate that the particles are still counted even after a time range when the number of particles reaches a peak. On the other hand, if the first feature amount X is smaller than the second feature amount Y, it may indicate that the particles are counted even before the time range when the number of particles reaches the peak. Further, if a difference between the first feature amount X and the second feature amount Y is large, it may indicate that the number of particles measured near the mode is dominant. On the contrary, if the difference between the two feature amounts is small, it may indicate that a ratio of the number of particles measured near the mode with respect to the total number of particles is small.

Thus, the condition changing unit 102 may first calculate the difference between the first feature amount X and the second feature amount Y, and then determines whether an absolute value of the difference exceeds a preset threshold value. Further, the condition changing unit 102 also determines a time range to which the value of the first feature amount X belongs, i.e., whether the value of the first feature amount X belongs to a time range of cleaning by the purge gas or a time range of cleaning by the application of a high voltage. Through this process, it may be possible to investigate the tendency of the particles adhering to the inside of the depressurized processing vessel 12, i.e., whether particles physically adhering to the depressurized processing vessel 12 and thus likely to be dispersed by a shock wave of a purge gas are dominant, or whether particles adhering to the depressurized processing vessel 12 by an electrostatic force and thus unlikely to be dispersed by the purge gas are dominant, i.e., whether particles likely to be dispersed by an electromagnetic stress are dominant.

Based on the tendency of the particles adhering to the inside of the depressurized processing vessel 12, conditions of the cleaning sequence in the cleaning unit 40 are changed. To be more specific, as shown in a table of FIG. 6, for example, the feature amounts X and Y and the contents of changes corresponding thereto are previously stored in the condition changing unit 102. Based on this table and the feature amounts X and Y, a supply amount of the purge gas and the number of application of the high voltage may be changed. In FIG. 6, a column of 'Small feature amount X' indicates a case where the value of the first feature amount X belongs to a time range before applying the high voltage, whereas a column of 'Large feature amount X' indicates a case where the value of the first feature amount X belongs to a time range after applying the high voltage. Likewise, the columns 'Small feature amount Y" and "Large feature amount Y" indicate time ranges before and after applying the high voltage, respectively, as in the cases of the feature amount X.

Further, in the present example embodiment, the contents of changes of the cleaning sequence are determined as follows. If the absolute value of the difference between the feature amounts X and Y is equal to or larger than the threshold value in the case of 'Small feature amount X,' particles to be dispersed by the purge gas may be dominant. However, since particles are also observed at a time other than the mode, the flow rate of the purge gas and the number of application of the high voltage may be both increased as compared to a standard case (the state of the cleaning sequence shown in FIG. 5). If the absolute value of the difference between the feature amounts X and Y is equal to or larger than the threshold value in the case of 'Large feature amount X,' particles to be dispersed by the application of the high voltage may be dominant. Thus, in this case, the number of application of the high voltage may be increased as compared to the standard case. Here, the flow rate of the purge gas may not be increased because, in general, the number of particles dispersed by the application of the high voltage is smaller than the number of particles dispersed by the purge gas, and an increase of the flow rate of the purge gas may not contribute to the cleaning of the processing vessel. Thus, in this case, the flow rate of the purge gas may be decreased, or the time of the cleaning sequence itself may be shortened by shortening the supply time of the purge gas.

Further, if the difference between the feature amounts X and Y is smaller than the threshold value in the case of 'Small feature amount X' and 'Small feature amount Y,' it may indicate that particles to be dispersed by the purge gas are dominant while particles to be dispersed by the application of the high voltage are hardly observed. Thus, only the flow rate of the purge gas may be increased as compared to the standard case. In this case, it may be also possible to decrease the number of application of the high voltage. If the difference between the feature amounts X and Y is smaller than the threshold value in the case of 'Large feature amount X"' and "Large feature amount Y,' it may indicate that particles to be dispersed by the application of the high voltage are dominant while particles to be dispersed by the purge gas are hardly observed. Thus, only the number of application of the high voltage may be increased as compared to the standard case. In this case, it may be also possible to decrease the flow rate of the purge gas or to shorten the supply time of the purge gas.

Further, if the difference between the feature amounts X and Y is smaller than the threshold value in the case of 'Small feature amount X' and 'Large feature amount Y' and, also, in the case of 'Large feature amount X' and 'Small feature amount Y,' the values of the feature amounts may be ranged over the time range of the purge gas and the time range of the application of the high voltage, and the difference between the feature amounts X and Y is small. Thus, it may not be easy to determine dominant particles. For the reason, in the present example embodiment, conditions of the cleaning sequence may not be changed. However, conditions shown in FIG. 6 themselves may be set as desired, without being limited to the present example embodiment. In FIG. 6, although the contents of changes are classified into, for example, eight cases based on the relationship between the first feature amount X and the second feature amount Y, the number of cases and the contents of changes of the cleaning sequence may be set as desired, without limited to the shown example.

Figure 7:
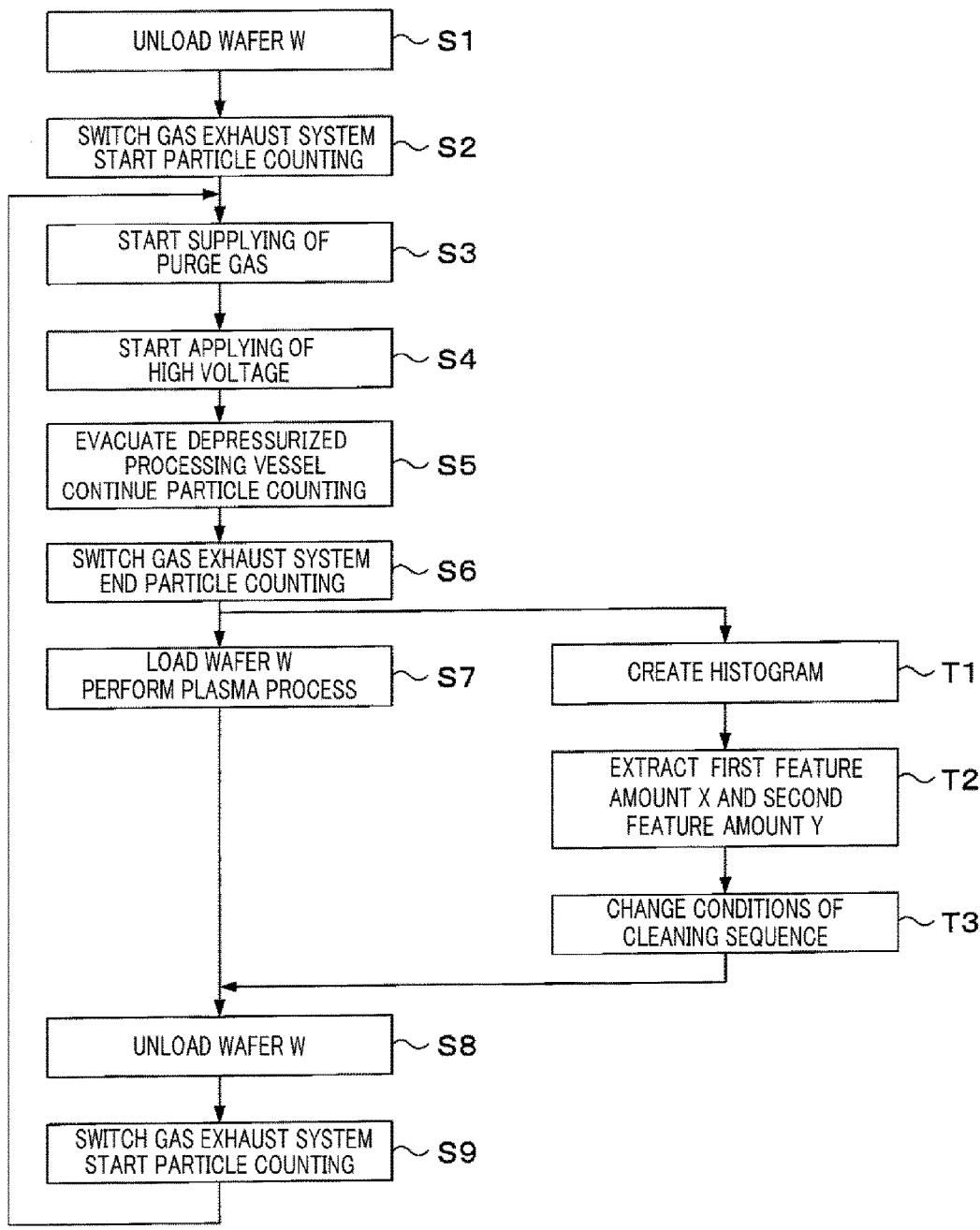
FIG. 7 is a flowchart for describing a process of a particle monitoring method.

The substrate processing system 10 in accordance with the present example embodiment has the configuration as described above. Now, a cleaning method and a particle monitoring method in the substrate processing system 10 will be explained. FIG. 7 is a flowchart showing example of major processes in the particle monitoring method.

As depicted in FIG. 7, if a wafer W is unloaded from the depressurized processing vessel 12 (block S1 of FIG. 7) after the processing of the wafer W is completed, the control valve 17a is closed and the bypass valve 17c is opened under the control of the controller 50. As a result, gas exhaust of the depressurized processing vessel 12 is switched to be performed through the bypass line 17b, and counting of particles by the particle monitor 18 is started (block S2 of FIG. 7).

Then, according to the cleaning sequence shown in FIG. 5, with the lapse of about 15 seconds after counting of the particles by the particle monitor 18 is started, the valve 34a provided downstream of the purge gas supplying unit 34 is opened, and a purge gas is supplied into the depressurized processing vessel 12 at a flow rate of, e.g., about 70 L/min (about 70000 SCCM) (block S3 of FIG. 7). As a result of the introduction of the purge gas, a shock wave is generated within the depressurized processing vessel 12, and particles physically adhering to the inside of the depressurized processing vessel 12 are dispersed. The dispersed particles are exhausted through the bypass line 17b and counted by the particle monitor 18. The counted number of the particles is inputted to the operation unit 100 via the controller 50.

Thereafter, with the lapse of about 7 seconds after the supply of the purge gas is begun, a high voltage is applied to the electrode 11a by the power supply 11b (block S4 of FIG. 7), so that particles within the depressurized processing vessel 12 are dispersed by an electromagnetic stress. The dispersed particles are exhausted through the bypass line 17b and counted by the particle monitor 18.

If the application of the high voltage is repeated preset number of times, a supply amount of the purge gas is reduced, and, subsequently, exhaust of the particles from the depressurized processing vessel 12 and the counting of the particles by the particle monitor 18 are continued (block S5 of FIG. 7).

Thereafter, the bypass valve 17c is closed, and the counting of the particles by the particle monitor 18 is terminated. Concurrently, the control valve 17a is opened, and a gas exhaust system is switched again and the gas exhaust of the depressurized processing vessel 12 is performed by the turbo pump 16b again (block S6 of FIG. 7). Further, while switching the gas exhaust system, a particle monitoring method by the particle monitoring system 1 is performed. The particle monitoring method by the particle monitoring system 1 will be described later in detail.

Subsequently, a new wafer W is loaded into the depressurized processing vessel 12, and a plasma process is performed (block S7 of FIG. 7). Then, upon the completion of the plasma process on the wafer W, the wafer W is unloaded from the depressurized processing vessel 12 (block S8 of FIG. 7). Thereafter, the gas exhaust system is switched again, and the counting of particles by the particle monitor 18 is begun (block S9 of FIG. 7). Afterward, cleaning of the inside of the depressurized processing vessel is performed, and the series of these processes are repeatedly performed.

Now, the aforementioned particle monitoring method will be elaborated.

If the counting of the particles by the particle monitor 18 is completed, a histogram showing a relationship between the number of particles and time, as depicted in FIG. 3, for example, is created in the operation unit 100 (block T1 of FIG. 7).

Then, based on the histogram, the first feature amount X and the second feature amount Y are calculated in the extracting unit 101 (block T2 of FIG. 7).

Thereafter, based on the correlation between the first feature amount X and the second feature amount Y, conditions of the cleaning sequence by the cleaning unit 40 are changed in the condition changing unit 102 (block T3 of FIG. 7). Then, if the plasma process on the wafer W is completed in the block S7 of FIG. 7 and the wafer W is unloaded from the depressurized processing vessel 12 (block S8 of FIG. 7), the gas exhaust system is switched again and counting of particles by the particle monitor 18 is begun (block S9 of FIG. 7). Then, cleaning of the inside of the processing vessel is performed according to the changed cleaning sequence.

In accordance with the above-described example embodiment, the histogram is created by counting the particles exhausted from the depressurized processing vessel 12 while the depressurized processing vessel 12 is being cleaned, and the first feature amount X and the second feature amount Y are calculated based on the histogram. Thus, it is possible to quantitatively investigate the tendency of the particles exhausted from the depressurized processing vessel 12 during the cleaning process of the depressurized processing vessel, i.e., whether particles to be dispersed by the shock wave of the purge gas are dominant or whether particles to be dispersed by the electromagnetic stress are dominant. Accordingly, it may be possible to appropriately monitor the particles within the depressurized processing vessel 12.

Further, by investigating the tendency of the dominant particles, the cleaning sequence can be optimized in the condition changing unit 102. Thus, it may be possible to clean the inside of the depressurized processing vessel 12 efficiently.

Moreover, in the above-described example embodiment, the conditions of the cleaning sequence are changed by the condition changing unit 102. However, as indicated by a dashed line in FIG. 2, for example, a display unit 103 which displays various kinds of information or through which an input to the controller 50 is conducted may be provided in the controller 50. By displaying the feature amounts X and Y on the display unit 103 in comparison, an operator may change the conditions of the cleaning sequence based on the displayed information. The display unit 103 may be implemented by a so-called graphical user interface including, but not limited to, a touch panel, a monitor or a liquid crystal display.

Furthermore, in the above-described example embodiment, the condition of the purge gas or the condition of the application of the high voltage is changed for the reference cleaning sequence shown in FIG. 5, for example. By way of example, the changed cleaning sequence may be stored in the condition changing unit 102, and conditions may be changed later for this changed cleaning sequence. That is, the changed cleaning sequence may be set as a reference sequence. The cleaning sequence to be used as a reference sequence may be set as desired.

Further, in the above example embodiment, it is described that if the difference between the first feature amount X and the second feature amount Y is small, the ratio of the number of particles counted near the mode with respect to the total number of particles is also small. Actually, however, even if particles are not counted except for near the peak, the difference between the two feature amounts X and Y may also be small. Although such a case occurs very unusually, a third feature amount Z as well as the first and second feature amounts X and Y may also be considered to exclude such a case, as will be described later. The third feature amount Z is a value indicating a ratio of the number of particles at a mode with respect to the total number of particles counted during a particle counting period. By considering this value, it is possible to determine whether the decrease of the difference between the feature amounts X and Y is resulted from concentration of particles near the mode. If it is determined that the particles are concentrated near the mode, conditions for the cleaning unit 40 may be set based on this.

Further, the number of the particles at the mode may also be considered. By way of example, even though it is found out that the particles are concentrated near the mode, if the number of the particles is smaller than that in the conventional case, both the flow rate of the purge gas and the number of application of the high voltage may be decreased.

The present example embodiment has been described for the case of investigating the tendency of the particles in the depressurized processing vessel 12 and changing the conditions for the cleaning of the depressurized processing vessel 12 to be performed after processing a next wafer W whenever processing of a wafer W is performed. Below, as a particle monitoring method in accordance with another example embodiment, a case of investigating a long-term tendency of particles in the depressurized processing vessel 12 will be explained.

Figure 8:
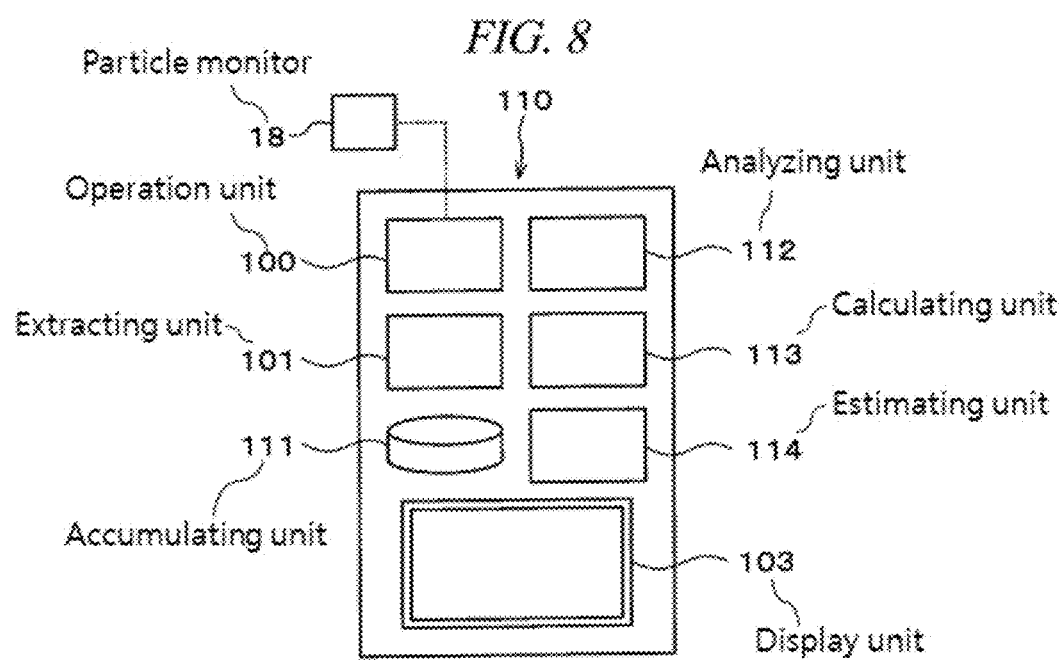
FIG. 8 is an explanatory diagram illustrating a schematic configuration of a controller in accordance with another example embodiment.

A controller 110 in accordance with this another example embodiment includes, in addition to the above-described operation unit 100 and the extracting unit 101, an accumulating unit 111 configured to store feature amounts calculated by the extracting unit 101; an analyzing unit 112 configured to conduct a principal component analysis for the feature amounts stored in the accumulating unit 111; a calculating unit 113 configured to calculate principal component scores from the analysis result of the analyzing unit 112 and the feature amounts stored in the accumulating unit 111; and an estimating unit 114 configured to estimate an adhesion state of particles within the depressurized processing vessel 12 based on a result of cluster analysis on the principal component scores, as illustrated in FIG. 8, for example. A particle monitoring system in accordance with the present example embodiment includes the respective units 100, 101, 111, 112, 113 and 114 and a particle monitor 18. Further, the controller 110 may also include the aforementioned display unit 103.

In the extracting unit 101 of the controller 110, a third feature amount Z represented by the equation (3) below is calculated instead of the aforementioned second feature amount Y.

$$Z = \frac{\text{MAX}(P_t)}{\sum_{i=0}^{T} P_t} \times 100 \quad (3)$$

In the equation (3), MAX($P_t$) denote the number of particles at a mode on a histogram.

As can be clearly seen from the equation (3), the third feature amount Z is a so-called peak ratio, i.e., a ratio of the number of particles at the mode with respect to the total number of particles counted during a particle counting period.

In the extracting unit 101, the feature amounts X and Z are calculated whenever wafer processes from block S1 to block S7 of FIG. 7 are repeated. The calculated feature amounts X and Z are stored in the accumulating unit 111.

The analyzing unit 112 conducts a principal component analysis by using the multiple number of feature amounts X and Z stored in the accumulation unit 111 as a variable, and calculates a principal component load for each of the first feature amount X and the third feature amount Z.

The calculating unit 113 calculates a principal component score for each of the feature amounts X and Z based on the principal component loads obtained by the analyzing unit 112 and the first and third feature amounts X and Z.

The estimating unit 114 conducts a cluster analysis for the principal component scores calculated by the calculating unit 113 and stratifies the principal component scores into plural clusters. Then, the estimating unit 114 investigates a characteristic of each cluster and estimates the state of particle adhesion within the depressurized processing vessel 12 for each cluster. Further, the respective units 112, 113 and 114 may be implemented by using, for example, general-purpose numerical analysis software.

As a specific example of estimating the state of particle adhesion within the depressurized processing vessel 12 by the analyzing unit 112, the calculating unit 113 and the estimating unit 114, there will be explained a case where the feature amounts X and Z are stored for each of samples 1 to 89, as shown in a table of FIG. 9. Cleaning is performed in time series in an ascending order of the samples. Further, the depressurized processing vessel 12 is opened and inspected between the samples 12 and 13, 32 and 33 and 48 and 49 of FIG. 9. Further, a part of components within the depressurized processing vessel 12 is replaced between the samples 12 and 13.

The analyzing unit 112 calculates a principal component load from each of the feature amounts X and Z stored in the accumulating unit 111. A first principal component load of the first feature amount X is about '0.7342,' and a second principal component load thereof is about '−0.6790.' Further, a principal component load of the third feature amount Z is calculated as an inclination of a straight line orthogonal to a straight line calculated from each principal component load of the first feature amount X. A first principal component load and a second principal component load of the third feature amount Z are about '0.7342' and about '0.6790,' respectively.

Figure 10:
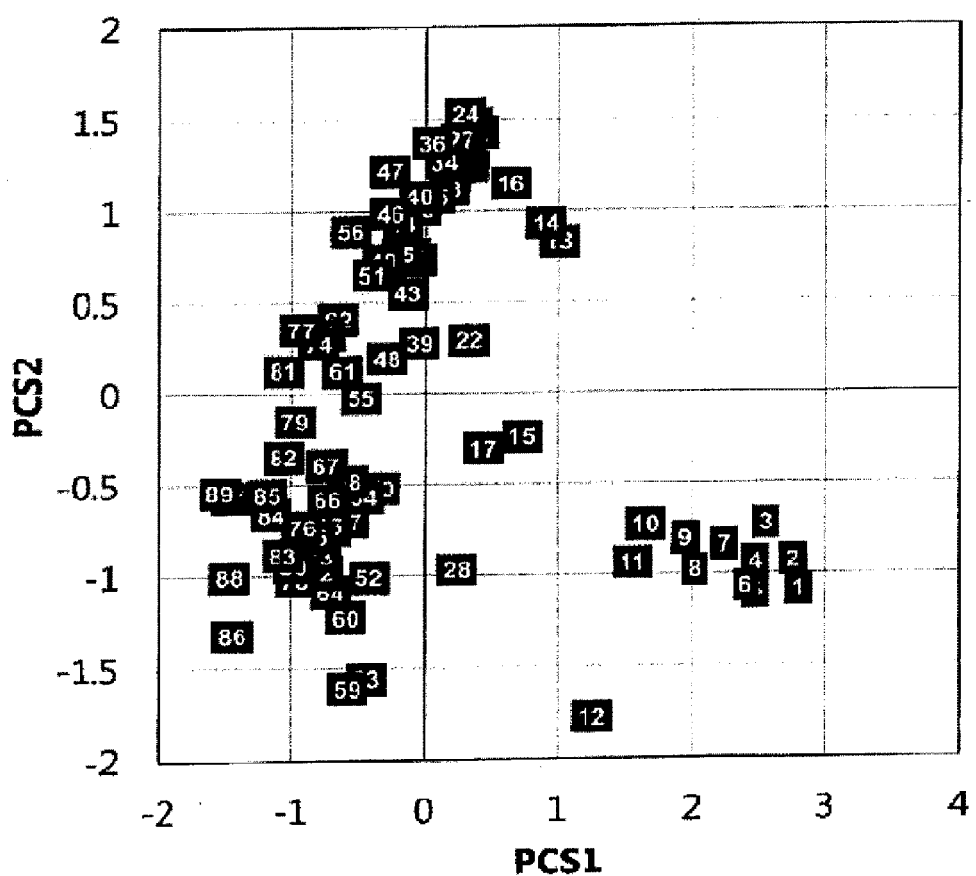
FIG. 10 is a scatter plot on which principal component scores are plotted.

Then, the calculating unit 113 calculates a first principal component score (PCS1 in FIG. 9) and a second principal component score (PCS2 of FIG. 9) for each of the samples 1 to 89 based on the principal component loads calculated by the analyzing unit 112 and the feature amounts X and Z. Then, the calculating unit 113 creates data, as illustrated in FIG. 10, by plotting the principal component scores of the samples 1 to 89. The numbers on the plot data of FIG. 10 correspond to the sample numbers shown in FIG. 9.

Figure 11:
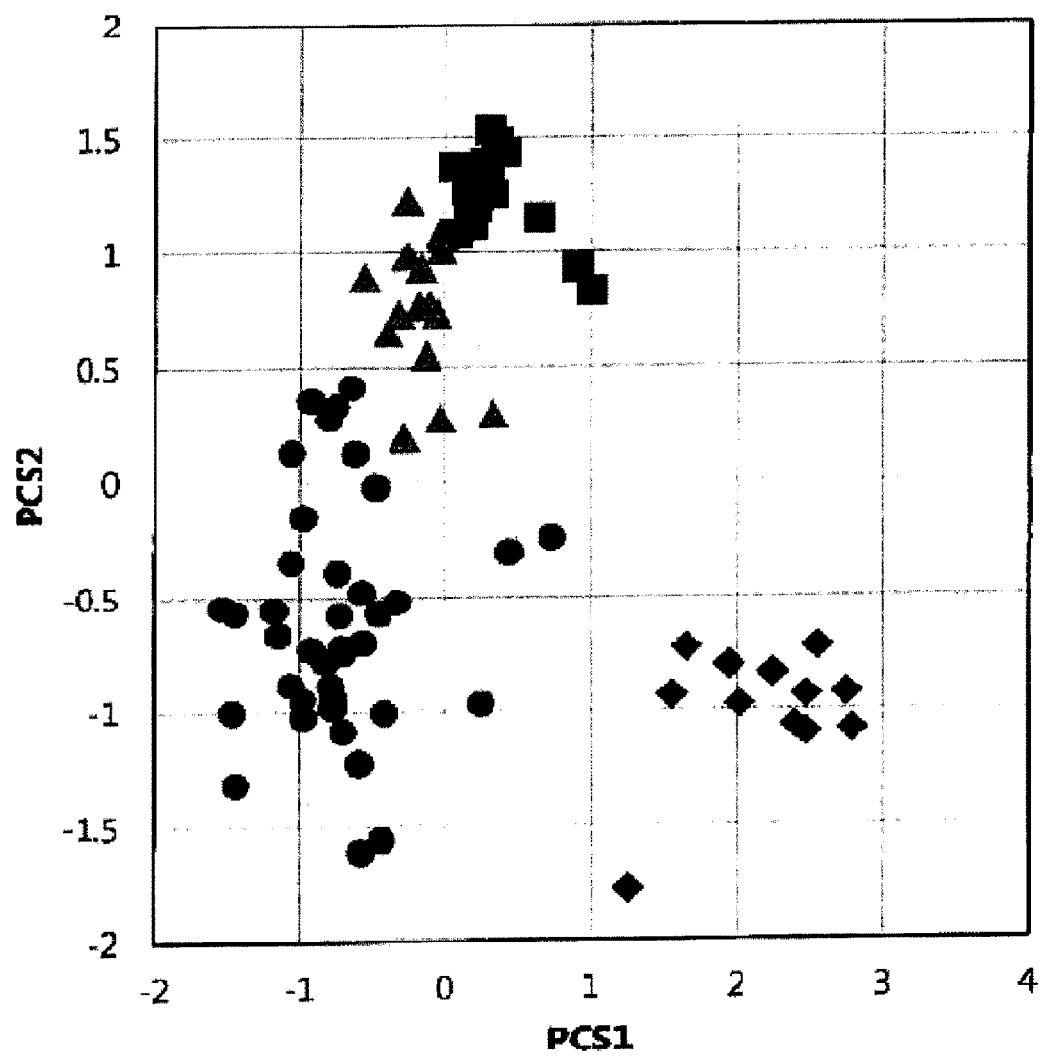
FIG. 11 is a scatter plot showing the principal component scores stratified into plural clusters.

The estimating unit 114 conducts a cluster analysis of the plot data obtained by the calculating unit 113 and stratifies the plot data into plural clusters, as illustrated in FIG. 11, for example. In the present example embodiment, the plot data is stratified into four clusters. The samples 1 to 12 belong to a first cluster; samples 13 to 32 belong to a second cluster; samples 33 to 48 belong to a third cluster; and samples 49 to 89 belong to a fourth cluster. Further, in FIG. 11, ◇ indicates the first cluster; □ indicates the second cluster; ∆ indicates the third cluster; and ○ indicates the fourth cluster.

Thereafter, the estimating unit 114 investigates a characteristic of each cluster and estimates a state of particle adhesion within the depressurized processing vessel 12 for each cluster. To elaborate, as for the first cluster, since the values of the first and third feature amounts X and Z are both very large, it may be determined that particles dispersed by the application of a high voltage in the later stage of the cleaning sequence are dominant or particles exhausted during the gas exhaust process of the depressurized processing vessel 12 in block S5 of FIG. 7 are dominant. Accordingly, the particles of the samples belonging to the first cluster are estimated to be caused by contamination of, e.g., the gas exhaust line 17 or the respective valves.

As for the second cluster, since the first feature amount X is very small, equivalent to a value immediately after the purge gas is supplied in the cleaning sequence, and since the third feature amount Z is very large, it may be determined that the particles dispersed by the purge gas in an earlier stage of the cleaning sequence are dominant. Thus, it is expected that a majority of particles of the samples belonging to the second cluster adhere to the inside of the depressurized processing vessel 12 physically. Further, as for the reason why the particles of the second cluster show different tendency from that of the particles of the first cluster, it is expected that dusts enter into the depressurized processing vessel from the outside when components of the depressurized processing vessel 12 are replaced between the samples 12 and 13.

As for the third cluster, the first feature amount X is larger than that of the second cluster, whereas the third feature amount Z is smaller than that of the second cluster. Accordingly, it may be determined that some of particles dispersed by the application of the high voltage are also counted, though particles dispersed by the purge gas are much more dominant.

As for the fourth cluster, the first feature amount X is larger than that of the third cluster and the third feature amount Z is smaller than that of the third cluster. In this case, it may be determined that particles are counted throughout the whole particle counting time, and some of particles dispersed by the purge gas are also counted, though particles dispersed by the application of the high voltage are much more dominant. Accordingly, it is expected that a majority of the particles of the samples belonging to the fourth cluster are dispersed by the application of the high voltage and are mainly resulted from contamination of the gas exhaust system. Further, from the result of the cluster analysis, it is found out that particles dispersed by the application of the high voltage become more dominant as the repetition number of the cleaning of the inside of the depressurized processing vessel 12 increases and that particles caused by the purge gas increases as a result of replacing the components when opening and inspecting the depressurized processing vessel 12.

According to the above-described example embodiment, the principal component scores are calculated based on the multiple feature amounts X and Z calculated by the extracting unit 101, and the state of particle adhesion within the depressurized processing vessel 12 is estimated based on the cluster analysis of the respective principal component scores. Therefore, it is possible to understand the long-term tendency of the particles within the depressurized processing vessel 12. As a result, it is possible to change sequence conditions such as increasing the number of the application of the high voltage and decreasing the supply time of the purge gas in the cleaning sequence whenever the processing of the wafer W is repeated preset number of times.

Further, typically, the wafer processing and the cleaning may be performed once a day by using, for example, a dummy wafer in order to check the state of particle adhesion to the wafer W or in order to analyze the components of the particles as stated above. Occasionally, the number of particles adhering to the dummy wafer may increase extremely for some reasons. In such a case, just by analyzing the particles on the dummy wafer, it may be difficult to determine whether the number of the particles has increased irregularly. In order to determine the irregularity, investigation of particles needs to be conducted again by using another dummy wafer. Since, however, the processing of the wafer W cannot be performed during such investigation by using the dummy wafers, throughput of the processing of the wafer W may be deteriorated. In such a case, if the long-term tendency is understood according to the particle monitoring method of the present example embodiment, it may be possible to determine whether the abnormality of the dummy wafer is irregular or not.

Further, in the above-described example embodiment, the condition changing unit 102 may be provided in the controller 110, and the cleaning sequence may be automatically changed based on the estimation result obtained by the estimating unit 114. In such a case, independently of the contents shown in the table of FIG. 6, the condition of the purge gas or the condition of the application of the high voltage may be changed, corresponding to dominant particles estimated through the cluster analysis.

Moreover, a display unit 103 may be provided in the controller 110, and each principal component score obtained by the cluster analysis, i.e., the contents shown in FIG. 11, may be displayed on the display unit 103, and the conditions for the cleaning sequence may be changed by an operator based on the displayed information.

In addition, in the above-described example embodiment, although the particle monitor 18 is provided at the bypass line 17b, the particle monitor 18 need not necessarily be provided at the bypass line 17b as long as particles from the depressurized processing vessel 12 can be counted. By way of example, the particle monitor 18 may be provided in the gas exhaust chamber 13a.

Further, in the above-described example embodiment, the first feature amount X is calculated by the equation (1). However, a mode of a histogram itself may be used as the first feature amount X, for example. In changing the conditions for the cleaning sequence, the tendency of particle distribution may be inspected by performing integration of the number of particles in left and right directions from the mode and then calculating time required until a ratio between the integration value and the total number of particles counted during the counting period reaches a preset value. The conditions for the cleaning sequence may be changed based on the tendency of the particle distribution and the mode.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

EXPLANATION OF CODES

1: Particle monitoring system
10: Substrate processing apparatus
11: Susceptor
12: Depressurized processing vessel
13: Main body
13a: Gas exhaust chamber
14: Microwave generator
15: Microwave supplying unit
16: Gas exhaust device
17: Gas exhaust line
18: Particle monitor
20: Supporting member
21: Microwave transmitting plate
22: Slot plate
23: Dielectric plate
24: Plate
25: Coaxial waveguide
26: Gas baffle plate
27: Supporting member
30: Gas supply opening
31: Gas supply line
33: Rare gas supply unit
34: Purge gas supply unit
50: Controller
100: Operation unit
101: Extracting unit 102: Condition changing unit
103: Display unit
110: Controller
111: Accumulating unit
112: Analyzing unit
113: Calculating unit
114: Estimating unit
W: Wafer

I claim:

1. A particle monitoring method of monitoring particles included in an exhaust gas from a depressurized processing vessel, in which a process is performed on a substrate, the particle monitoring method comprising:
cleaning an inside of the depressurized processing vessel by dispersing the particles through processes of supplying a purge gas into the depressurized processing vessel to apply a shock wave, and then, supplying a high voltage intermittently to apply an electromagnetic stress to the depressurized processing vessel;
counting the particles included in the exhaust gas from the depressurized processing vessel while cleaning the inside of the depressurized processing vessel by a counting unit;
creating a histogram showing a relationship between time and the number of the particles from a result of the counting of the particles;
extracting, from the histogram, a first feature amount indicating a correlation between the most frequent value of the number of the particles and a particle counting period;
extracting, from the histogram, a second feature amount indicating a correlation between the particle counting period and a distribution tendency of the particles whether particles dispersed by the shock wave of the purge gas are dominant or whether particles dispersed by the electromagnetic stress are dominant during the particle counting period; and
changing a condition for the cleaning of the inside of the depressurized processing vessel based on the distribution tendency of the particles.

2. The particle monitoring method of claim 1,
wherein the first feature amount is calculated by a following equation, $$X = \frac{\sum_{i=0}^{T} t \times P_t}{\sum_{i=0}^{T} P_t}$$

the second feature amount is calculated by a following equation, and $$Y = \frac{\sum_{i=0}^{T} t \times D(t)}{\sum_{i=0}^{T} D(t)} \left( \begin{array}{c|c} P_t = 0 & D(t) = 0 \\ P_t > 0 & D(t) = 1 \end{array} \right)$$

X denotes the first feature amount; T denotes the particle counting period; t denotes a measurement time; $P_t$ denotes the number of the particles at the measurement time; and Y denotes the second feature amount.

3. The particle monitoring method of claim 1,
wherein a difference between the first feature amount and the second feature amount is calculated, and
the condition for the cleaning of the inside of the depressurized processing vessel is changed based on a relationship between the difference and a preset threshold value, and a correlation between the first feature amount and the second feature amount.

4. The particle monitoring method of claim 3,
wherein the condition for the cleaning of the inside of the depressurized processing vessel is at least one of a condition of supplying the purge gas and a condition of intermittently applying the high voltage.

5. The particle monitoring method of claim 1,
wherein the extracted first feature amount and the extracted second feature amount are displayed on a display unit.

6. A particle monitoring method of monitoring particles included in an exhaust gas from a depressurized processing vessel, in which a process is performed on a substrate, the particle monitoring method comprising:
cleaning an inside of the depressurized processing vessel by dispersing the particles through processes of supplying a purge gas into the depressurized processing vessel to apply a shock wave, and then, supplying a high voltage intermittently to apply an electromagnetic stress to the depressurized processing vessel;
counting the particles included in the exhaust gas from the depressurized processing vessel while cleaning the inside of the depressurized processing vessel by a counting unit;
creating a histogram showing a relationship between time and the number of the particles from a result of the counting of the particles;
extracting, from the histogram, a first feature amount indicating a correlation between the most frequent value of the number of the particles and a particle counting period;
extracting, from the histogram, a second feature amount indicating a correlation between the total number of the particles counted during the particle counting period and the number of the particles at the most frequent value;
performing the extracting of the first feature amount and the extracting of the second feature amount whenever the process is performed on the substrate in the depressurized processing vessel;
calculating a principal component load of each of the first feature amount and the second feature amount by performing a principal component analysis in which the first feature amount and the second feature amount are set as variables;
calculating a principal component score of each of the first feature amount and the second feature amount based on each principal component load;
performing a cluster analysis for the principal component scores and estimating a state of particle adhesion within the depressurized processing vessel based on a result of the performing of the cluster analysis; and
changing a condition for the cleaning of the inside of the depressurized processing vessel based on a result of the estimating of the state of particle adhesion.

7. The particle monitoring method of claim 6,
wherein the first feature amount is calculated by a following equation, $$X = \frac{\sum_{i=0}^{T} t \times P_t}{\sum_{i=0}^{T} P_t}$$

the second feature amount is calculated by a following equation, and $$Z = \frac{\text{MAX}(P_t)}{\sum_{i=0}^{T} P_t} \times 100$$

X denotes the first feature amount; T denotes the particle counting period; t denotes a measurement time; $P_t$ denotes the number of the particles at the measurement time; Z denotes the second feature amount; and MAX ($P_t$) denotes the number of the particles at the most frequent value.

8. The particle monitoring method of claim 6, wherein the principal component scores obtained after the performing of the cluster analysis are plotted to be displayed on a display unit.

9. A particle monitoring system of monitoring particles included in an exhaust gas from a depressurized processing vessel, in which a process is performed on a substrate, the particle monitoring system comprising:
a counting unit configured to count the particles included in the exhaust gas from the depressurized processing vessel while cleaning the inside of the depressurized processing vessel by dispersing particles through processes of supplying a purge gas into the depressurized processing vessel to apply a shock wave, and then, supplying a high voltage intermittently to apply an electromagnetic stress to the depressurized processing vessel;
an operation unit configured to create a histogram showing a relationship between time and the number of the particles from a result of the counting of the particles;
an extracting unit configured to extract, from the histogram, a first feature amount indicating a correlation between the most frequent value of the number of the particles and a particle counting period, and configured to extract, from the histogram, a second feature amount indicating a correlation between the particle counting period and a distribution tendency of the particles whether particles dispersed by the shock wave of the purge gas are dominant or whether particles dispersed by the electromagnetic stress are dominant during the particle counting period.

10. The particle monitoring system of claim 9, wherein the first feature amount is calculated by a following equation, $$X = \frac{\sum_{i=0}^{T} t \times P_t}{\sum_{i=0}^{T} P_t}$$

the second feature amount is calculated by a following equation, and $$Y = \frac{\sum_{i=0}^{T} t \times D(t)}{\sum_{i=0}^{T} D(t)} \left( \begin{array}{l|l} P_t = 0 & D(t) = 0 \\ P_t > 0 & D(t) = 1 \end{array} \right)$$

X denotes the first feature amount; T denotes the particle counting period; t denotes a measurement time; $P_t$ denotes the number of the particles at the measurement time; and Y denotes the second feature amount.

11. The particle monitoring system of claim 9, further comprising:
a condition changing unit configured to calculate a difference between the first feature amount and the second feature amount, and configured to change a condition for the cleaning of the inside of the depressurized processing vessel based on a relationship between the difference and a preset threshold value, and a correlation between the first feature amount and the second feature amount.

12. The particle monitoring system of claim 11, wherein the condition for the cleaning of the inside of the depressurized processing vessel is at least one of a condition of supplying the purge gas and a condition of intermittently applying the high voltage.

13. The particle monitoring system of claim 9, further comprising:
a display unit configured to display the extracted first feature amount and the extracted second feature amount.

14. A particle monitoring system of monitoring particles included in an exhaust gas from a depressurized processing vessel, in which a process is performed on a substrate, the particle monitoring system comprising:
a counting unit configured to count the particles included in the exhaust gas from the depressurized processing vessel while cleaning the inside of the depressurized processing vessel by dispersing particles through processes of supplying a purge gas into the depressurized processing vessel to apply a shock wave, and then, supplying a high voltage intermittently to apply an electromagnetic stress to the depressurized processing vessel;
an operation unit configured to create a histogram showing a relationship between time and the number of the particles from a result of the counting of the particles;
an extracting unit configured to extract, from the histogram, a first feature amount indicating a correlation between the most frequent value of the number of the particles and a particle counting period, and configured to extract, from the histogram, a second feature amount indicating a correlation between the total number of the particles counted during the particle counting period and the number of the particles at the most frequent value;
an analyzing unit configured to calculate a principal component load of each of the first feature amount and the second feature amount by performing a principal component analysis in which the first feature amount and the second feature amount extracted whenever the process is performed on the substrate in the depressurized processing vessel are set as variables;
a calculating unit configure to calculate a principal component score of each of the first feature amount and the second feature amount based on each principal component load; and an estimating unit configured to perform a cluster analysis of for the principal component scores and estimate a state of particle adhesion within the depressurized processing vessel based on a result of the cluster analysis.

15. The particle monitoring system of claim 14, wherein the first feature amount is calculated by a following equation, $$X = \frac{\sum_{i=0}^{T} t \times P_t}{\sum_{i=0}^{T} P_t}$$

the second feature amount is calculated by a following equation, and $$Z = \frac{\text{MAX}(P_t)}{\sum_{i=0}^{T} P_t} \times 100$$

X denotes the first feature amount; T denotes the particle counting period; t denotes a measurement time; $P_t$ denotes the number of the particles at the measurement time; Z denotes the second feature amount; and MAX $(P_t)$ denotes the number of the particles at the most frequent value.

16. The particle monitoring system of claim 14, further comprising:
a display unit configured to display the principal component scores obtained after the cluster analysis by being plotted.

* * * * *